United States Patent [19]

Forder

[11] Patent Number: 5,389,114
[45] Date of Patent: Feb. 14, 1995

[54] METHOD OF TREATING AND USING WASTE PRODUCTS

[76] Inventor: David E. Forder, 33 Clifton Road, Regents Park, Southampton SO1 4GY, United Kingdom

[21] Appl. No.: 39,176

[22] Filed: Apr. 16, 1993

[30] Foreign Application Priority Data

Oct. 19, 1990 [GB] United Kingdom ............. 9022725

[51] Int. Cl.$^6$ ............................................. C10L 5/00
[52] U.S. Cl. ................................ 44/552; 44/311; 44/491; 44/590; 44/628; 210/748; 210/751
[58] Field of Search ............ 44/552, 311, 628, 491, 44/590; 210/748, 751

[56] References Cited

U.S. PATENT DOCUMENTS

| 1,453,988 | 5/1923 | Mueller | 44/590 |
| 4,290,269 | 9/1981 | Hedstrom . | |
| 4,592,291 | 6/1986 | Sullivan | 110/346 |
| 4,749,496 | 7/1988 | Reischl | 210/692 |
| 5,125,931 | 6/1992 | Schulz | 44/552 |

FOREIGN PATENT DOCUMENTS

| 0058128 | 8/1982 | European Pat. Off. . |
| 0271628 | 12/1986 | European Pat. Off. . |
| 3418101 | 12/1985 | Germany . |
| 3226798 | 1/1994 | Germany . |
| 2119813 | 5/1982 | United Kingdom . |

OTHER PUBLICATIONS

Poffe et al. "Disinfection of effluents from Municipal Sewage Treatment Plants with Peroxy Acid", Zentralbl.
Bakteriol., Parasitenkd., Infektionskr. Hyg., Abt. 1: Orig., Reihe B, 167 (4) 337–46.

Primary Examiner—Stephen Kalafut
Assistant Examiner—Cephia D. Toomer
Attorney, Agent, or Firm—Shoemaker and Mattare Ltd.

[57] ABSTRACT

A method of treating and using waste products and to products produced thereby is described. The method comprises agitating the sewage sludge mixture and waste products with a co-agent to bind the mixture in a mixing chamber (1) having paddles (2). The mixture is fed via a controlled feed (3) to a worm pump (4) leading to the base of cyclone (5) where it is broken down into a coarse particles using air from a blower fan (6). The coarse particled mixture is passed to a cyclone dryer/disinfector (7) for sterilisation by steam from an injector (8). The treated sludge mixture may be fed via a hopper (9) to an auger press (10) from which it is extruded and passed for radiation and sterilisation in a microwave oven (12) and then cut into bricketts. Alternatively, the treated sludge mixture can be passed to hopper (16) via a controlled feed (17) to plank molds (19). The moulds pass under a press (20) to form bio-degradable planks (21) for building shuttering.

9 Claims, 1 Drawing Sheet

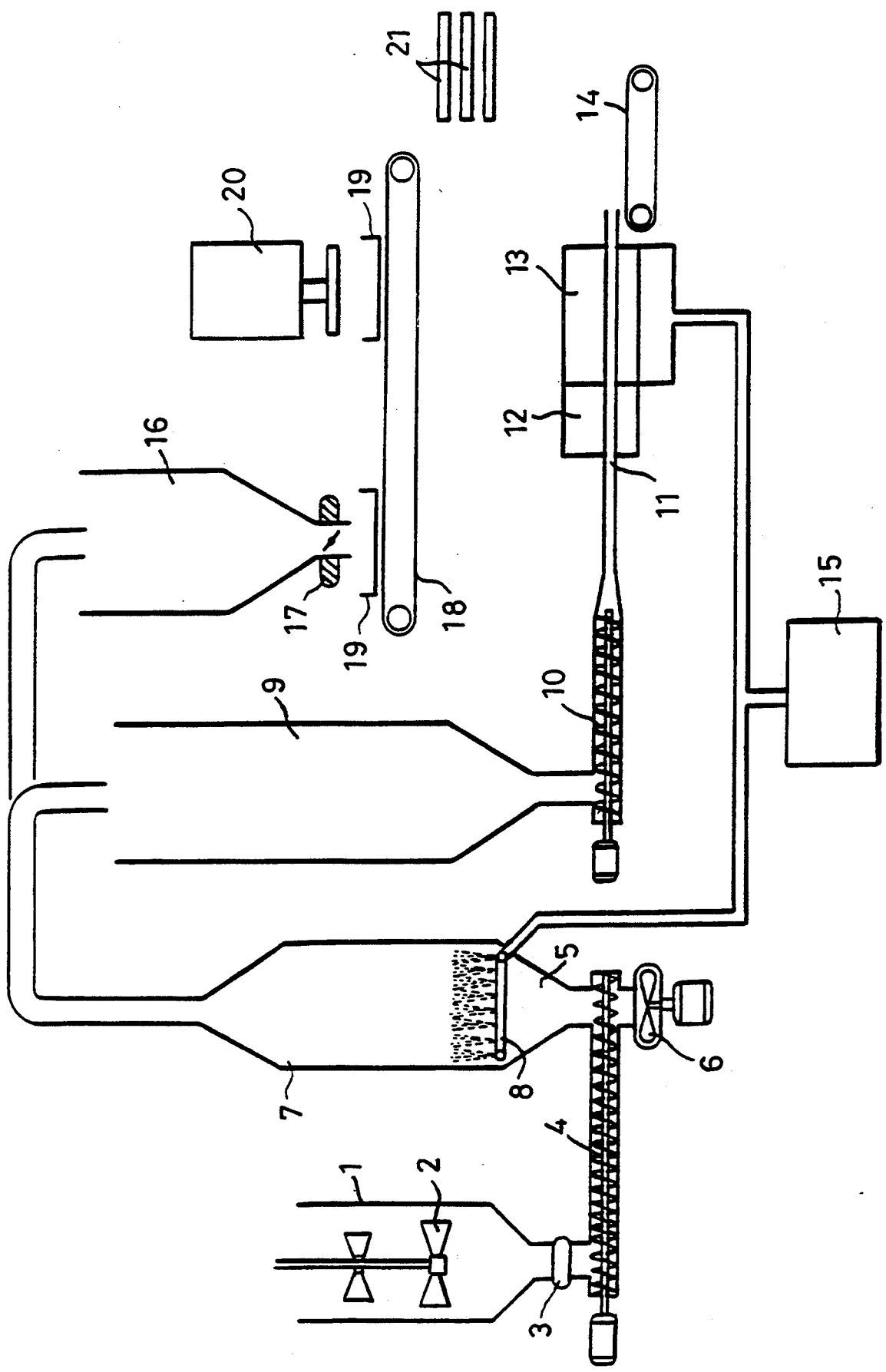

METHOD OF TREATING AND USING WASTE PRODUCTS

This invention relates to a method of treating and using waste products and to products produced thereby.

Waste products such as sewage sludge has hitherto been disposed of by dumping .at sea, used as landfil or is incinerated. However, because of recent legislation to reduce pollution of the atmosphere the known methods of disposal are restricted or are no longer available.

An aim of the present invention is to provide a method of treating sewage sludge and to recycle the resultant product in a useful and economic form which avoids pollution to the atmosphere.

According to one aspect of the present invention there is provided a method of treating sewage sludge solution by mixing it with a co-agulant to bind the mixture, pressing it to remove moisture, adding at least one waste product to the sludge solution, agitating the mixture and extruding and shaping it to the required size wherein it further comprises the step of heating and drying the extruded product and placing it in a microwave oven to radiate the extruded product.

Conveniently, two waste products are added to the sludge solution in the following proportions:

75% sludge cake;
12.5% mushroom peat
12.5% sawdust to provide a combustible product.

Preferably, the cake mixture is fed through a worm pump to the base of a cyclone where it is broken down to a coarse particulate material by blowing air across it and injecting steam to sterilise the product.

According to another aspect of the present invention there is provided a product of the above mentioned method in brickett form for use as a fuel.

According to a further aspect of the present invention there is provided a product of the above mentioned method which is pressed into planks or rectangular panels for use as bio-degradable shuttering.

Embodiments of the present invention will now be described, by way of example, with reference to the accompanying drawing, which shows a diagrammatic layout of a manufacturing plant for treating sewage sludge, according to the invention.

According to the method of treating the sewage sludge solution, the sludge containing 95% water is removed from the treatment beds and an acetic acid co-agulant is added to bind the sludge solution. One suitable co-agulant is that sold under The Trade Name ZETAG57. The sludge solution and binder are then treated in a roller press to produce a cake containing 25% water. The treated sewage sludge in the form of a cake is added to other waste products such as mushroom peat and sawdust in the following proportions:

75% sewage sludge cake
12.5% mushroom peat
12.5% sawdust.

The aggregate is agitated in a mixing chamber 1 having paddles 2 and fed via a controlled feed 3 to a worm pump 4 to the base of a cyclone 5 where it is broken down into coarse particles of approximately 2 to 3 mm outside diameter by blowing air across it using a blower fan 6. The coarse particle mixture is passed to a cyclone dryer and disinfector 7 where it is sterilised by injecting steam into the coarse particulate mixture via a steam injector 8 to moisten and form a doughy mixture.

The sterilised sludge mixture is collected in a hopper 9 to which a paracetic acid is added such as that sold under the Trade Name 'OXYMASTER' to disinfect the sludge mixture. The mixture is fed to an auger press 10 which reduces the moisture content and forces the mixture through an extrusion tube 11 where it emerges in the form of a sausage shape. The extrusion is then passed to a final section comprising a microwave oven 12 and a cooling chamber 13 where it is microwaved to stabilise and again sterilise the finished product prior to drying and cooling. The finished product, which can be used as a commercial or domestic fuel, is then cut into briquettes and transported by a conveyor 14 to a packing station.

The fuel briquettes may be used to heat a furnace 15 for supplying the steam to the steam injector 8 and to the drying section.

The treated sludge mixture, instead of being fed to the hopper 9 may be fed to a hopper 16 to which the OXYMASTER disinfecter is added together with a suitable resin to bind the mixture. The mixture is then fed via a controlled feed 17 onto a plank mould conveyor 18. The plank moulds 19 pass under a steam press 20 which compresses the pre-treated sludge mixture into bio-degradable planks 21 or alternatively rectangular panels for use as building shuttering. The use of the bio-degradable shuttering may replace timber for building concrete or concrete reinforced structures. The bio-degradable planks disintigrate and are absorbed into the surrounding soil, thus reducing the amount of timber hitherto used for the purpose and to reduce the cost. Alternatively the planks may be removed when the concrete is set and brokendown for recyling in the plank forming cycle of the manufacturing plant.

TESTING

Tests have been undertaken to analyse:
Test A—Initial sewage samples for levels of bacteria;
Test B—To test the results of combustion of a fuel sample.

| Test A - on three sterilised sewage sludge samples | | |
| --- | --- | --- |
| Sample | Contents | Total Viable Count/g |
| Chickenhall Sludge Sample B | Sewage Sludge + Waste Product Mixture | $5.0 \times 10^3$ |
| Chickenhall Sludge Sample D | Sewage Sludge + Farm Waste Mixture | $3.6 \times 10^3$ |
| Chickenhall Sludge Sample F | Sewage Sludge + Farm Waste + Disinfectant Mixture | $7.4 \times 10^3$ |
| Chickenhall Sludge Sample A | Sewage Sludge | $4.1 \times 10^8$ |
| Chickenhall Sludge Sample C | Sewage Sludge + Farm Waste | $2.2 \times 10^8$ |
| Chickenhall Sludge Sample E | Sewage Sludge + Farm Waste + Disinfectant | $16 \times 10^9$ |
| Chickenhall Sludge Sample Z | Sewage Sludge | $16 \times 10^9$ |

The method of treatment and the products produced by the method have the following advantages.

Test B
CHEMISTRY LABORATORY POWERGEN PLC -
ANALYTICAL REPORT NO. 3957

| Pressed Sewage Sludge | | Date: 10 07 90 | |
|---|---|---|---|
| Moisture, | as received | % | 16.05 |
| Ash Content | Dry basis | % | 2.67 |
| Gross C V KJ/KG | Dry basis | | 22.000* |
| *Ash Analysis by Edax No-STD | | | |
| Sulphur | as SO3 | % | 36.1 |
| Calcium | as CAO | % | 40.4 |
| Manganaese | as NN304 | % | 3.9 |
| Iron | as FE203 | % | 19.6 |

*Estimated figure - incomplete combustion.

The products are manufactured from a base ingredient which can be a health hazard, if not properly disposed of and can, even after treatment, cause pollution to the atmosphere. The present invention overcomes these problems by safely and economically recycling an unwanted by-product.

In its form as a fuel product it provides a useful form of economical energy which is clean and light in weight to handle is non-pollutant either during combustion or in the disposal of the residue.

The fuel produced according to the invention, although in limited quantity, is an economical alternative in protecting the natural energy resources for future generations and provides a major contribution to reducing the effect of a present day pollutant.

In an alternative use of the product produced by method according to the present invention viz as a biodegradable form of building shuttering, the amount of timber required for this purpose is considerably reduced thus protecting the natural standing timber, both for environmental reasons and for future generations.

Although two uses of the treated product have been described, it will be apparent that the treated sewage sludge may have other applications where a bio-degradable material is required.

I claim:

1. A method of treating sewage sludge comprising steps of
   mixing the sludge with a coagulant to bind the sludge then,
   pressing it to remove moisture,
   adding at least one waste product to the sludge then, agitating the mixture,
   extruding and shaping the sludge to produce an extruded product, and then
   heating and drying the extruded product and irradiating it in a microwave oven.

2. A method as claimed in claim 1, wherein the coagulant is acetic acid.

3. A method as claimed in claim 2, wherein two waste products are added to the sludge cake mixture in the following proportions:
   75% sewage sludge
   12.5% mushroom peat
   12.5% sawdust
   to provide a combustion product.

4. A method as claimed in claim 1, wherein the mixture is fed through a worm pump to the base of a cyclone where it is broken down into a coarse particulate material by blowing air across it and injecting steam to sterilize the product.

5. A method as claimed in claim 4, wherein the sterilized particulate sludge product is fed to a hopper and disinfected to kill harmful bacteria in the sludge mixture.

6. A method as claimed in claim 5, wherein the disinfected mixture is fed by an auger feed and is extruded as a sausage shape and cut into briquettes.

7. A product of the method claimed in claim 5, wherein the finished product is a fuel briquette.

8. A method as claimed in claim 5, wherein the disinfected mixture is fed via a controlled feed to molds and to a press to form planks or rectangular panels.

9. A product of the method claimed in claim 8, wherein the finished product is pressed into planks or rectangular panels.

* * * * *